US00PP35592P2

(12) United States Plant Patent
Winslow

(10) Patent No.: US PP35,592 P2
(45) Date of Patent: Jan. 16, 2024

(54) LOBELIA PLANT NAMED 'WNLOBLSB23'

(50) Latin Name: *Lobelia erinus*
Varietal Denomination: WNLOBLSB23

(71) Applicant: Benjamin K. Winslow, Austin, TX (US)

(72) Inventor: Benjamin K. Winslow, Austin, TX (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 18/135,168

(22) Filed: Apr. 16, 2023

(51) Int. Cl.
*A01H 5/02* (2018.01)
*A01H 6/26* (2018.01)

(52) U.S. Cl.
USPC ..... Plt./451

(58) Field of Classification Search
USPC ..... Plt./451

CPC . A01H 5/02; A01H 5/00; A01H 6/268; A01H 6/26

See application file for complete search history.

(56) References Cited

U.S. PATENT DOCUMENTS

PP15,526 P2 * 2/2005 Oud ..... A01H 6/268 Plt./451
PP32,655 P2 * 12/2020 Winslow ..... A01H 5/02 Plt./451

* cited by examiner

*Primary Examiner* — June Hwu
(74) *Attorney, Agent, or Firm* — C. Anne Whealy

(57) ABSTRACT

A new and distinct cultivar of *Lobelia* plant named 'WNLOBLSB23', characterized by its compact, upright to outwardly spreading and mounding to trailing plant habit; vigorous and sturdy growth habit; freely branching habit; dense and bushy plant form; freely flowering habit; long flowering period; bright purplish blue to light violet-colored flowers with white-colored centers; relative high temperature tolerance; and good container and garden performance.

2 Drawing Sheets

Figure 1:
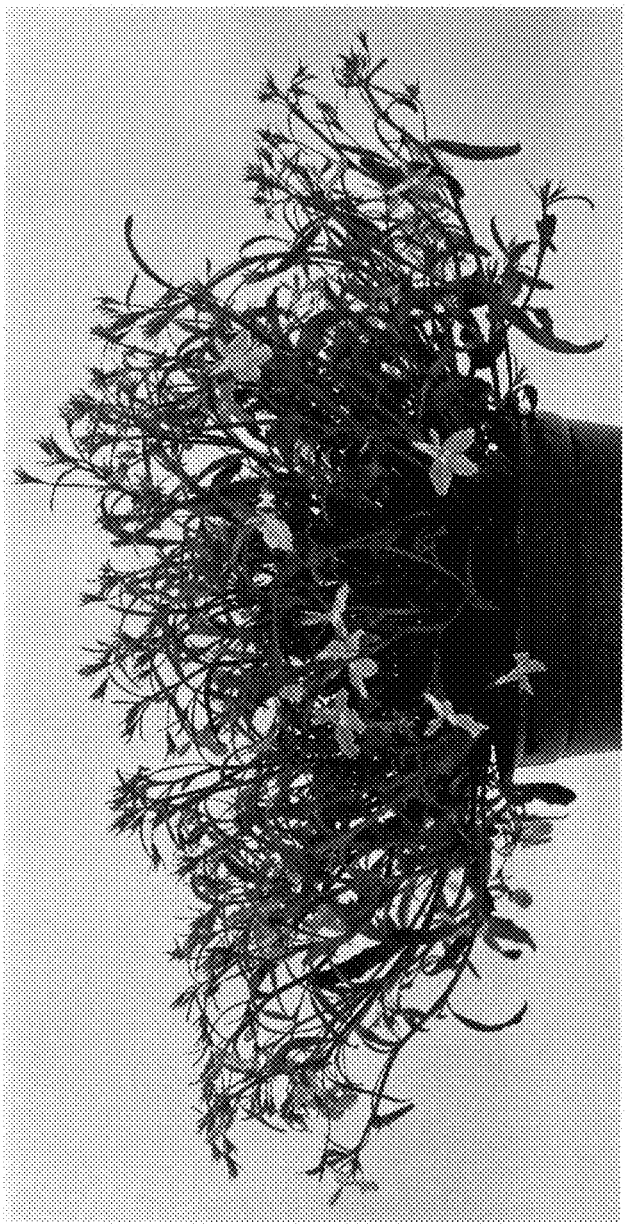

Botanical designation: *Lobelia erinus.*
Cultivar denomination: 'WNLOBLSB23'.

BACKGROUND OF THE INVENTION

The present invention relates to a new and distinct cultivar of *Lobelia* plant, botanically known as *Lobelia erinus* and hereinafter referred to by the name 'WNLOBLSB23'.

The new *Lobelia* plant is a product of a planned breeding program conducted by the Inventor in Alajuela, Costa Rica and Carleton, Michigan. The objective of the breeding program is to create new vigorous and freely-branching *Lobelia* plants with a long flowering period, high temperature tolerance and good garden performance.

The new *Lobelia* plant originated from a cross-pollination made by the Inventor in Alajuela, Costa Rica on May 17, 2017 of a proprietary selection of *Lobelia erinus* identified as code number LOB-0009, not patented, as the female, or seed, parent with *Lobelia erinus* 'KLELE11769', disclosed in U.S. Plant Pat. No. 24,037, as the male, or pollen, parent. The new *Lobelia* plant was discovered and selected by the Inventor as a single flowering plant within the progeny of the stated cross-pollination in a controlled greenhouse environment in Carleton, Michigan on Nov. 2, 2018.

Asexual reproduction of the *Lobelia* plant by vegetative terminal cuttings in Carleton, Michigan since Nov. 7, 2018 has shown that the unique features of this new *Lobelia* plant are stable and reproduced true to type in successive generations.

SUMMARY OF THE INVENTION

Plants of the new *Lobelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNLOBLSB23'. These characteristics in combination distinguish 'WNLOBLSB23' as a new and distinct *Lobelia* plant:

1. Compact, upright to outwardly spreading and mounding to trailing plant habit.
2. Vigorous and sturdy growth habit.
3. Freely branching habit; dense and bushy plant form.
4. Freely flowering habit.
5. Long flowering period.
6. Bright purplish blue to light violet-colored flowers with white-colored centers.
7. Relatively high temperature tolerant.
8. Good container and garden performance.

Plants of the new *Lobelia* differ primarily from plants of the female parent selection in the following characteristics:

1. Plants of the new *Lobelia* have larger flowers than plants of the female parent selection.
2. Flowers of plants of the new *Lobelia* are bright purplish blue to light violet in color whereas flowers of plants of the female parent selection are white in color.
3. Plants of the new *Lobelia* are more high temperature tolerant than plants of the female parent selection.

Plants of the new *Lobelia* differ primarily from plants of the male parent, 'KLELE11769', in the following characteristics:

1. Plants of the new *Lobelia* are more vigorous than plants of 'KLELE11769'.
2. Plants of the new *Lobelia* are more freely branching than plants of 'KLELE11769'.
3. Flowers of plants of the new *Lobelia* are bright purplish blue to light violet in color whereas flowers of plants of 'KLELE11769' are white in color.
4. Plants of the new *Lobelia* are more high temperature tolerant than plants of 'KLELE11769'.

Plants of the new *Lobelia* can be compared to plants of *Lobelia erinus* 'WNLOLASKBL', disclosed in U.S. Plant Pat. No. 32,655. In side-by-side comparisons, plants of the new *Lobelia* differ primarily from plants of 'WNLOLASKBL' in the following characteristics:

1. Plants of the new *Lobelia* are more upright than and not as prostrate as plants of 'WNLOLASKBL'.
2. Plants of the new *Lobelia* are more vigorous than plants of 'WNLOLASKBL'.
3. Plants of the new *Lobelia* have smaller flowers than plants of 'WNLOLASKBL'.
4. Plants of the new *Lobelia* are more high temperature tolerant than plants of 'WNLOLASKBL'.

BRIEF DESCRIPTION OF THE PHOTOGRAPHS

The accompanying colored photographs illustrate the overall appearance of the new *Lobelia* plant showing the colors as true as it is reasonably possible to obtain in colored reproductions of this type. Colors in the photographs may differ slightly from the color values cited in the detailed botanical description which accurately describe the actual colors of the new *Lobelia* plant.

The photograph on the first sheet (FIG. 1) is a side perspective view of a typical flowering plant of 'WNLOBLSB23' grown in a container.

Figure 2:
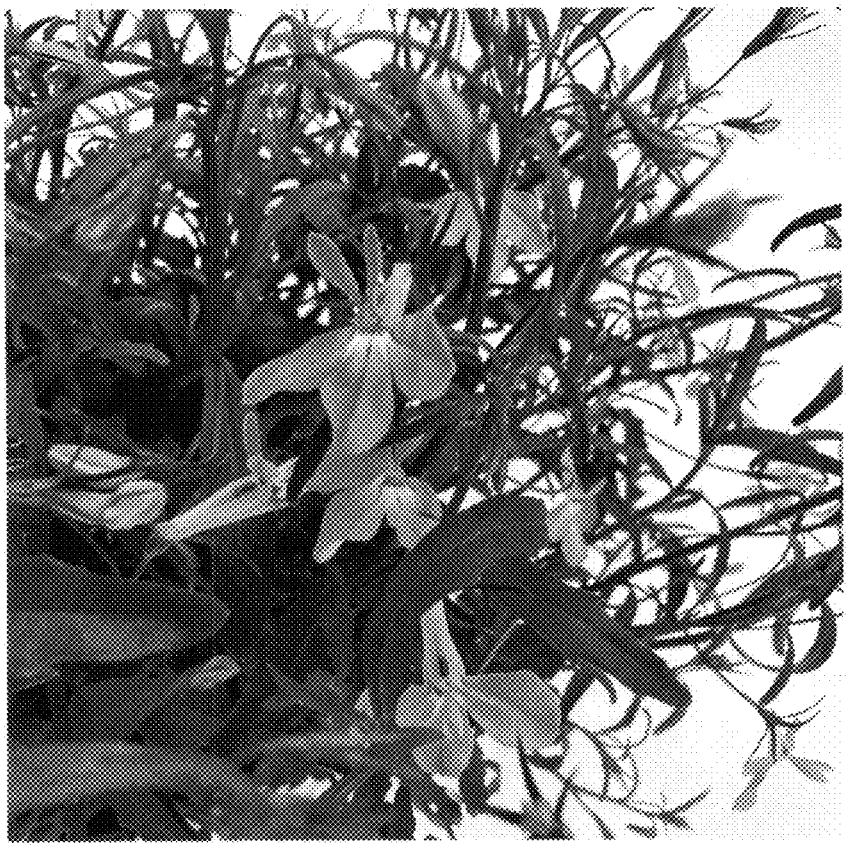

The photograph on the second sheet (FIG. 2) is a close-up view of a typical flowering plant of 'WNLOBLSB23'.

DETAILED BOTANICAL DESCRIPTION

The aforementioned photographs and following observations and measurements describe plants grown during the summer in 740-ml containers in an acrylic-covered greenhouse in Carlton, Michigan and under cultural practices typical of commercial *Lobelia* production. During the production of the plants, day temperatures ranged from 18 C to 32 C and night temperatures ranged from 18 C to 24 C. Plants were ten weeks from planting rooted cuttings when the photographs and description were taken. In the following description, color references are made to The Royal Horticultural Society Colour Chart, 2015 Edition, except where general terms of ordinary dictionary significance are used.

Botanical classification: *Lobelia erinus* 'WNLOBLSB23'.

Parentage:

*Female, or seed, parent.*—Proprietary selection of *Lobelia erinus* identified as code number LOB-0009, not patented.

*Male, or pollen, parent.*—*Lobelia erinus* 'KLELE11769', disclosed in U.S. Plant Pat. No. 24,037.

Propagation:

*Type cutting.*—Vegetative terminal cuttings.

*Time to initiate roots, summer.*—About seven to twelve days at ambient temperatures about 28 C.

*Time to initiate roots, winter.*—About 10 to 14 days at ambient temperatures about 20 C.

*Time to produce a rooted young plant, summer.*—About three to four weeks at ambient temperatures about 28 C.

*Time to produce a rooted young plant, winter.*—About four to five weeks at ambient temperatures about 20 C.

*Root description.*—Fine, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Compact, upright to outwardly spreading and mounding to trailing plant habit; freely branching habit with lateral branches developing at potentially every node; dense and bushy plant habit; vigorous and sturdy growth habit and rapid growth rate.

*Plant height.*—About 13 cm.

*Plant width.*—About 38 cm.

*Lateral branch description.*—Length: About 22 cm. Diameter: About 2 mm. Internode length: About 2.5 cm. Strength: Strong, flexible. Aspect: Upright to outwardly spreading to trailing. Texture and luster: Smooth, glabrous; somewhat glossy. Color: Close to 146A.

Leaf description:

*Arrangement.*—Alternate, simple.

*Length.*—About 4.75 cm.

*Width.*—About 1.3 cm.

*Shape.*—Oblong; slightly recurved and twisting with development.

*Apex.*—Acute.

*Base.*—Cuneate.

*Margin.*—Dentate with widely-spaced "teeth"; not undulate.

*Texture and luster, upper and lower surfaces.*—Smooth, glabrous; somewhat glossy.

*Venation pattern.*—Pinnate.

*Color.*—Developing leaves, upper surface: More green than 146A. Developing leaves, lower surface: Close to 146A. Fully expanded leaves, upper surface: Close to between 146A and 147A; venation, close to between 146A and 147A. Fully expanded leaves, lower surface: Close to 146A to 146B; venation, close to 146A to 146B.

*Petioles.*—Length: About 5 mm. Diameter: About 3 mm. Texture and luster: Smooth, glabrous; somewhat glossy. Color, upper surface: Close to 146A. Color, lower surface: Close to 146A to 146B.

Flower description:

*Flower arrangement, habit and shape.*—Single, flowers axillary or terminal; flowers face mostly outwardly; freely flowering habit with flowers potentially developing at every axil; flowers bilabiate with two upper petals and three larger fused lower petals.

*Fragrance.*—None detected.

*Natural flowering season.*—Long flowering period, in Michigan, plants of the new *Lobelia* flower continuously from planting in the spring until frost in the autumn; early flowering habit, plants begin flowering about seven weeks after planting.

*Flower longevity on the plant*.—Longevity of individual flowers is highly dependent on temperature, flowers typically last about one to two weeks on the plant; flowers persistent.

*Flower diameter*.—About 1.5 cm by 1.75 cm.

*Flower depth*.—About 1.5 cm.

*Flower throat diameter*.—About 4 mm.

*Flower tube length*.—About 9 mm to 10 mm.

*Flower tube diameter, distally*.—About 4 mm.

*Flower tube diameter, proximally*.—About 2 mm.

*Flower buds*.—Length: About 7 mm. Diameter: About 3 mm. Shape: Oblong. Color, developing sepals: Close to 144B to 144C.

*Petals*.—Arrangement: Single whorl of five petals fused towards the base; two upper petals and three larger fused lower petals. Upper petals: Lobe length, beyond throat: About 7 mm. Lobe width, beyond throat: About 2.5 mm. Shape: Oblanceolate. Apex: Cuspidate to mucronate. Margin: Entire; not undulate. Texture and luster, upper and lower surfaces: Smooth, glabrous; matte. Color, when opening, upper surface: Close to 97A; venation, close to 97A. Color, when opening, lower surface: Close to 97B; venation, close to 97B. Color, fully opened, upper surface: Close to between 91A and 92B; venation, close to between 91A and 92B; color becoming closer to between 91B and 92C with subsequent development. Color, fully opened, lower surface: Close to between 91C and 92C; venation, close to between 91C and 92C; color becoming closer to between 91D and 92D with subsequent development. Lower petals: Lobe length, beyond throat: About 1 cm. Lobe width, beyond throat: About 6.5 mm. Shape: Obovate. Apex: Rounded to acute to slightly cuspidate. Margin: Entire; not undulate. Texture and luster, upper and lower surfaces: Smooth, glabrous; matte. Color, when opening, upper surface: Close to 97A; venation, close to 97A. Color, when opening, lower surface: Close to 97B; venation, close to 97B. Color, fully opened, upper surface: Close to between 91A and 92B; towards the throat, close to NN155D with nectar guides, close to N144A; venation, close to between 91A and 92B; color becoming closer to between 91D and 92D with subsequent development. Color, fully opened, lower surface: Close to between 91B and 92B; venation, close to between 91B and 92B; color becoming closer to between 91C and 92C with subsequent development. Color, throat: Close to 97D; spots, close to 93B. Color, tube: Close to between 91A and 92A.

*Sepals*.—Arrangement: Single whorl of five sepals, fused at the base; star-shaped calyx. Length: About 7.5 mm. Width: About 1 mm. Shape: Acicular. Apex: Acute. Margin: Entire; not undulate. Texture and luster, upper and lower surfaces: Smooth, glabrous; slightly glossy. Color, upper and lower surfaces: Close to 146A.

*Peduncles*.—Length: About 2.5 cm. Diameter: Less than 1 mm. Strength: Strong, flexible; wiry. Aspect: About 45 degrees from lateral branch axis. Texture and luster: Smooth, glabrous; somewhat glossy. Color: Close to between 146A and 147A.

*Reproductive organs*.—Stamens: To date, stamen development has not been observed on plants of the new *Lobelia*. Pistils: Quantity per flower: One. Pistil length: About 7.5 mm. Stigma shape: Globose. Stigma color: Close to N187A. Style color: Close to 144D. Ovary color: Close to 144A to 144B.

*Fruits and seeds*.—To date, fruit and seed development have not been observed on plants of the new *Lobelia*.

Pathogen & pest resistance: To date, plants of the new *Lobelia* have not been noted to be resistant to pathogens and pests common to *Lobelia* plants.

Garden performance: Plants of the new *Lobelia* have been observed to have good garden performance and to tolerate wind, rain and to be relatively tolerant to high temperature conditions.

It is claimed:

1. A new and distinct *Lobelia* plant named 'WNLOBLSB23' as illustrated and described.

* * * * *